United States Patent
Sheperak

(10) Patent No.: US 9,993,282 B2
(45) Date of Patent: Jun. 12, 2018

(54) PLASMA DIRECTED ELECTRON BEAM WOUND CARE SYSTEM APPARATUS AND METHOD

(76) Inventor: Thomas J. Sheperak, Swanton, OH (US)

( * ) Notice: Subject to any disclaimer, the term of this patent is extended or adjusted under 35 U.S.C. 154(b) by 260 days.

(21) Appl. No.: 14/117,119

(22) PCT Filed: May 10, 2012

(86) PCT No.: PCT/US2012/037249
§ 371 (c)(1),
(2), (4) Date: Jun. 27, 2014

(87) PCT Pub. No.: WO2012/158443
PCT Pub. Date: Nov. 22, 2012

(65) Prior Publication Data
US 2014/0303549 A1    Oct. 9, 2014

Related U.S. Application Data

(60) Provisional application No. 61/485,747, filed on May 13, 2011.

(51) Int. Cl.
*A61B 18/18* (2006.01)
*A61B 18/04* (2006.01)
*A61N 5/10* (2006.01)
*H05H 1/46* (2006.01)
*A61N 1/44* (2006.01)

(52) U.S. Cl.
CPC ............ *A61B 18/042* (2013.01); *A61N 1/44* (2013.01); *A61N 5/10* (2013.01); *H05H 1/46* (2013.01); *A61N 2005/1089* (2013.01); *H05H 2001/466* (2013.01); *H05H 2001/4682* (2013.01); *H05H 2240/20* (2013.01); *H05H 2245/122* (2013.01)

(58) Field of Classification Search
CPC ........ A61B 18/042; A61B 2018/00452; A61B 2018/1213; A61B 2018/122; A61N 1/44
See application file for complete search history.

(56) References Cited

U.S. PATENT DOCUMENTS

| | | | |
|---|---|---|---|
| 3,648,015 A | 3/1972 | Fairbairn |
| 3,947,654 A | 3/1976 | Fairbairn |
| 4,504,526 A | 3/1985 | Hofer et al. |
| 4,647,818 A | 3/1987 | Ham |

(Continued)

FOREIGN PATENT DOCUMENTS

| | | |
|---|---|---|
| EP | 1693014 B1 | 1/2009 |
| GB | 2458329 A | 9/2009 |
| WO | 9417835 A1 | 8/1994 |

OTHER PUBLICATIONS

PCT International Search Report, Application No. PCT/US2012/037249, dated Jan. 25, 2013.

(Continued)

*Primary Examiner* — Michael Peffley
*Assistant Examiner* — Amanda Zink
(74) *Attorney, Agent, or Firm* — MacMillan, Sobanski & Todd, LLC

(57) ABSTRACT

A plasma generating device that utilizes a cold plasma to contain and direct a stream of electrons with a hand held nozzle to enhance healing of wounds and skin surface abnormalities, and to kill pathogens on skin surfaces in humans and animals wounds, abnormalities and pathogens.

22 Claims, 6 Drawing Sheets

(56) References Cited

U.S. PATENT DOCUMENTS

| | | | |
|---|---|---|---|
| 4,652,763 A | 3/1987 | Nablo | |
| 4,766,287 A | 8/1988 | Morrisroe et al. | |
| 5,214,263 A | 5/1993 | Sakuragi | |
| 5,383,019 A | 1/1995 | Farrell et al. | |
| 5,414,267 A | 5/1995 | Wakalopulos | |
| 5,578,831 A | 11/1996 | Hershcovitch | |
| 6,002,096 A | 12/1999 | Hoffelner et al. | |
| 6,298,806 B1 | 10/2001 | Moisan et al. | |
| 6,475,215 B1* | 11/2002 | Tanrisever | H05H 1/24 606/32 |
| 6,629,974 B2 | 10/2003 | Penny et al. | |
| 6,723,091 B2* | 4/2004 | Goble | A61B 18/042 606/34 |
| 7,022,121 B2 | 4/2006 | Stern et al. | |
| 7,578,818 B2 | 8/2009 | Platt | |
| 7,628,787 B2 | 12/2009 | Sartor et al. | |
| 7,674,713 B2 | 3/2010 | Johnston et al. | |
| 7,880,119 B2 | 2/2011 | Reddy et al. | |
| 8,030,849 B2* | 10/2011 | Suslov | A61B 18/042 315/111.01 |
| 8,920,361 B2* | 12/2014 | Staack | B05D 1/62 604/24 |
| 8,979,838 B2* | 3/2015 | Woloszko | A61B 18/042 606/34 |
| 2004/0116918 A1* | 6/2004 | Konesky | A61B 18/042 606/34 |
| 2004/0186470 A1 | 9/2004 | Goble et al. | |
| 2006/0027539 A1 | 2/2006 | Golkowski | |
| 2006/0084158 A1 | 4/2006 | Viol | |
| 2006/0189974 A1 | 8/2006 | Penny et al. | |
| 2006/0189976 A1* | 8/2006 | Karni | A61B 18/042 606/41 |
| 2009/0012589 A1 | 1/2009 | Watson | |
| 2010/0130911 A1 | 5/2010 | Morfill et al. | |

OTHER PUBLICATIONS

Ehlbeck et al., "Low Temperature Atmospheric Pressure Plasma Sources for Microbial Decontamination", Journal of Physics D: Applied Physics, 2011, vol. 44, pp. 1-33.

Extended European Search Report, Application No. EP12785098.0 dated Apr. 4, 2014.

Israeli Office Action, Application No. 229386 dated Dec. 1, 2016.

* cited by examiner

PLASMA DIRECTED ELECTRON BEAM WOUND CARE SYSTEM APPARATUS AND METHOD

BACKGROUND OF THE INVENTION

This invention relates in general to plasma generating devices and in particular to the use of a hybrid plasma device for treatment of skin wounds.

Some prior art plasma devices generally operate at relatively high voltage and current levels. As a result, such prior art devices may well damage skin as an attempt is made to use one to treat a wound surface. In some cases, prior art plasma devices generate Ultra violet wavelengths which also may damage skin. Additionally, prior art plasma devices utilize an arc or induction to ionize a gas which requires complicated configurations, close tolerances and component wear. Accordingly, a low power, single electrode and simple plasma device that could be adapted for wound treatment would be desirable.

SUMMARY OF THE INVENTION

The present invention relates to a plasma generating device that uses a unique means to create a cold, non-thermal plasma to enhance healing of wounds and skin surface abnormalities, and to kill pathogens on skin surfaces in humans and animals. The invention utilizes a cold plasma to contain and direct a stream of electrons and photons to such wounds, abnormalities and pathogens and contemplates a portable hand-held apparatus to accomplish those purposes. The invention also contemplates a method for the use of such system and apparatus to accomplish those purposes.

The present invention contemplates a system that includes an electrode for establishing a shaped plasma for directing an electron beam. A gas supply is connected to the electrode to support the plasma. The system also includes a voltage supply connected to the electrode for energization of the plasma and establishment of the electron beam.

The present invention also contemplates a method for treating wounds that includes providing the system described above and then energizing the electrode to establish a Plasma Directed Electron Beam (PDEB) and to create a supply of photons that are guided within the plasma. The PDEB is then directed toward a wound.

Various objects and advantages of this invention will become apparent to those skilled in the art from the following detailed description of the preferred embodiment, when read in light of the accompanying drawings.

DETAILED DESCRIPTION OF THE PREFERRED EMBODIMENT

Figure 1:
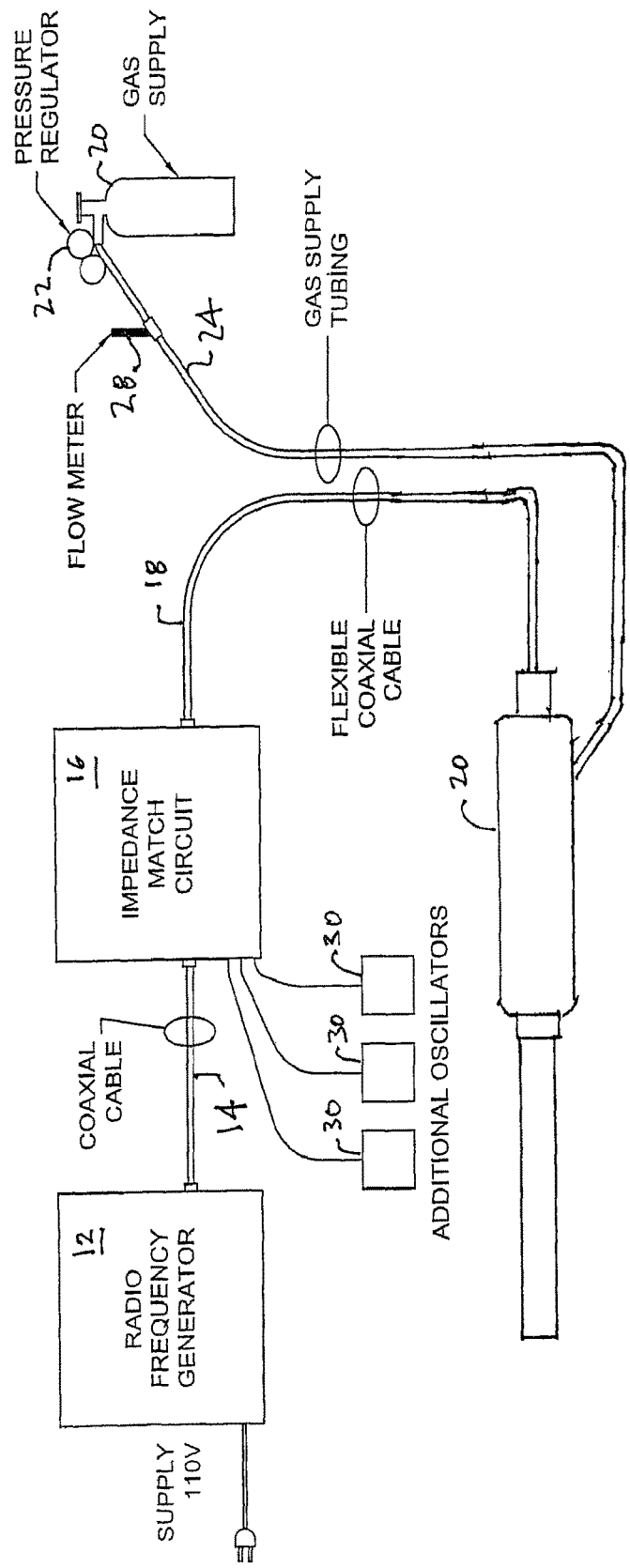
FIG. 1 is illustrates a Plasma Directed Electron Beam (PDEB) system that is in accordance with the present invention.

Unlike prior art plasma devices which energize (ionize) gases through arc or induction, the Plasma Directed Electron Beam (PDEB) system uses the electrical potential from a single electrode to generate sufficient plasma to serve as a waveguide sheath for the transmission of a coherent, non-axially propagating electromagnetic wave. The high energy density electromagnetic wave, coupled with the non-thermal plasma waveguide sheath, provide the singularly distinct advantages of this technology. Rather than relying on the chemical reaction caused by the ions and radicals in a plasma to change the chemical composition of the components of a wound, the PDEB dissociates certain materials to permit a safe recombination. Simply put, electricity travels through the plasma guide to provide the desired function.

The single electrode emission of a plasma guided coherent electromagnetic wave simplifies the configuration of the delivery device in contrast to the prior art plasma devices, eliminating the need for a critically aligned cathode and anode or geometrical accuracy for the induction circuitry. The present invention, and the accompanying improvements and discoveries create the ability to operate at power ranges between 5 Watts and 30 Watts with simplified circuitry, non-critical geometrical alignments and long component life. This invention produces a cold, non-thermal plasma to serve as the waveguide for a radio frequency beam that directs emitted electrons to the intended target, hence the name, Plasma Directed Electron Beam (PDEB). The benefits of this cold plasma waveguide are, among others, that the beam produced by the apparatus, when directed to the skin of a recipient, causes no discomfort, pain or burns, permitting the PDEB to pass across the wound area and healthy tissue without discomfort to the recipient or damage to healthy skin tissue.

The present invention utilizes a flexible cable attached between the output of the impedance matching circuitry and the hand held apparatus. Refined tuning procedures permit this lower power operation with micro-currents and permit the use of a flexible conductor which can extend a distance from the tuning network enabling the portability of the handheld wound care device.

Additionally, with the present invention, the radio frequency wave can be "time shared" in that the PDEB can be emitted from multiple apertures along a conductor and along parallel paths or a circular path, simultaneously, from a single conductor and single source of energy. This phenomena utilizes the properties of a linearly propagating wave form, in that the wave extends out from the source and back to the source, in this case, oscillating at 13.56 million times per second. When the conductor with multiple apertures is located at and along the virtual high voltage point of the wave (peak voltage), providing sufficient voltage to create a plasma and being approximately one meter in virtual length, each aperture, whether via a tubular electrode or just a hole in a hollow conductor, will produce the PDEB, simultaneously. This is accomplished with little additional power input for the reason that as the waveform extends outbound, the high voltage potential strikes a plasma and emits electrons at the closest aperture along the conductor, then continuing to move outbound, the voltage potential strikes a plasma and emits electrons at the next aperture, continuing outbound accomplishing the same striking a plasma and emitting electrons at each successive aperture location along the conductive path. This phenomenon is sequential and yet appears simultaneous at all apertures at once. In this instance the peak voltage on the waveform is on and off at 13.56 million times a second, a speed which the human eye cannot detect causing the appearance of all apertures operating at the same time.

Referring now to the drawings, there is illustrated in FIG. 1 a Plasma Directed Electron Beam (PDEB) system 10. The system 10 includes a radio frequency generator 12 connected by a coaxial cable 14 to the impedance matching circuitry box 16. A second coaxial cable 18 connects the impedance matching box 16 to a PDEB generator 20. The PDEB generator 20 is connected to an inert gas supply 22 by gas supply tubing 24. The gas supply includes a pressure regulator 26 to maintain a constant pressure for the gas being supplied to the PDEB generator 20. Additionally, a flow meter 28 may be included to monitor the gas usage. The system 10 may also include one of more additional oscillator units 30 to provide additional resonant frequencies to the apparatus; however, the inclusion of such additional oscillator units is optional.

Figure 2:
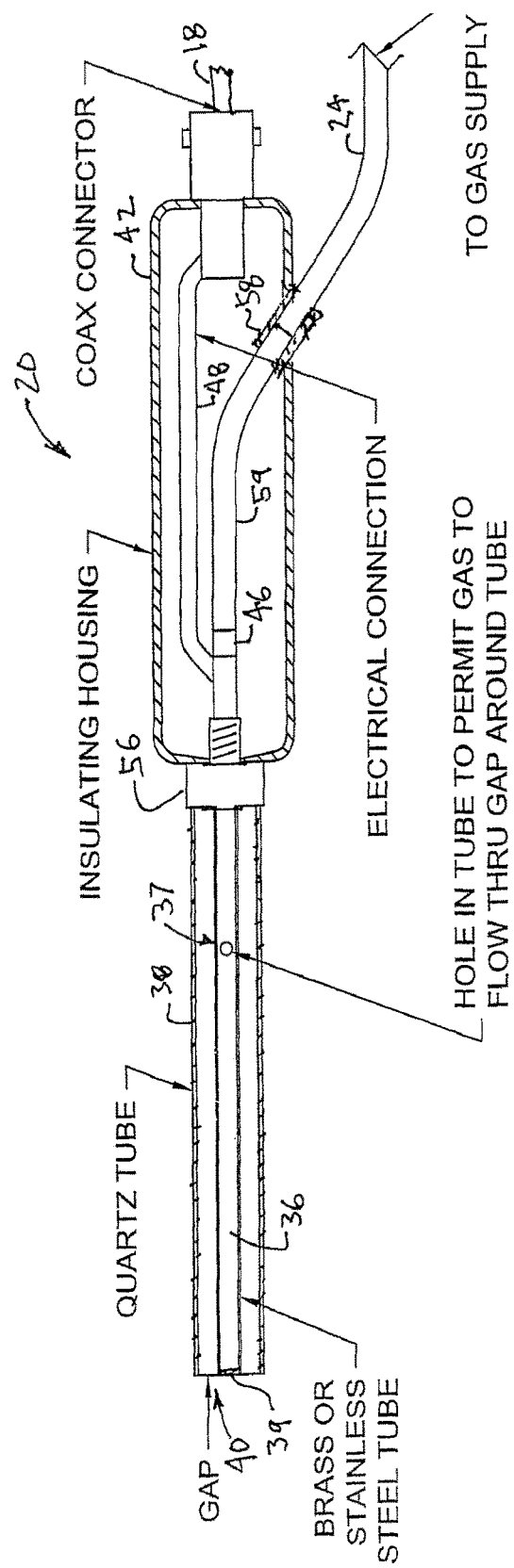
FIG. 2 is sectional view of a first embodiment of a PDEB generator that is included in the system shown in FIG. 1.

A sectional view of the PDEB generator 20 is shown in FIG. 2. As shown in the figure, the PDEB generator 20 includes a hollow straight tube electrode 36 that may be fabricated from brass, stainless steel or a similar material. The electrode 36 is axially disposed within a cylindrical quartz tube 38. While a quartz tube is illustrated in FIG. 2, it will be appreciated that the invention also may be practiced with a tube formed from any other similar nonconductive material, such as, for example glass or plastic. One end of the electrode 36 that is contained within the generator 20 is connected to the gas supply tubing 24 while the other end is sealed by a cap 39. The straight tube electrode 36 has at least one aperture 37 formed through its surface to permit the flow of the introduced gas through both the tube electrode and the surrounding gap 40 formed between the electrode 36 and the quartz tube 38. The gas flows in a laminar manner to establish a waveguide. The electrode 36 and quartz tube 38 are mounted upon, and extend from, an insulated housing 42. The insulated housing also carries a coaxial connector 44 for attachment of the second coaxial cable 18 that carries the incoming radio frequency energy. A connector 46 is provided to connect the gas supply tube 24 to the open end of the electrode 36. Electrical connections 46 are disposed within the housing 42 to electrically connect the radio frequency energy to the electrode 36.

The inventor has successfully built and operated a PDEB system having the specific design features described in following paragraphs.

The housing 42, or shell, of the PDEB generator 20 is fabricated from an insulating material which should provide shielding to contain the RF energy or other electrical energy within the housing. The material must be dense enough to prohibit the infusion or growth of pathogens on the surface. The nozzle/electrode configuration were formed from 3/32 inch brass tubing 36 as the electrode and surrounded by with quartz tubing 38. The electrode is approximately 2 inch long. A preferred inside diameter for the quartz tubing 38 is 1/8 inch with a 1/32 inch annular gap around the electrode 36 to confine and direct the gas in a laminar flow. Generally, the gap width should be about half of the diameter of the aperture formed in the electrode tubing; however, larger or smaller gaps may be utilized. The quartz tubing 38 is cut to be flush with the tip of the electrode 36. The electrode 36 is press fit into a hole drilled into the top of a large head 8-32 screw 56. The quartz tubing 38 is then centered around the brass electrode 36 and attached to the head of the screw 56 with an adhesive so as to provide an airtight seal. An aperture (not shown) hole is drilled into the side of the brass tubing electrode 36 at about ½ inch from the point that tubing is press fit into the screw 56. The aperture provides for gas flow between the brass and quartz tubes. While one aperture was used in the prototype, it will be appreciated that the invention also may be practiced with a plurality of apertures formed through the brass tubing forming the electrode 36.

A coaxial cable 18 of adequate length is the preferable conductive media to convey the RF energy from the impedance matching circuit 16 to the hand held PDEB generator 20. As the present, a radio frequency of 13.56 MHz is used that represents a wavelength of about 20 meters. A coaxial cable length of two feet was arbitrarily utilized; however, given that the high voltage peak on a 20 meter wave can easily be about 1 meter, the coaxial cable may also be approximately one meter long. The length of the coaxial cable will affect the tuning in the impedance matching circuit 16. Coaxial cable mimics capacitance; therefore, compensating inductance and capacitance must be adjusted accordingly, either manually and/or automatically. The coaxial cable may be connected to the PDEB generator 20 by means of a coaxial connector 44 mounted upon the receiving end of the PDEB generator housing 42. A BNC connector was used in the prototype.

A conductive path is provided within the housing 42 for the radio frequency energy to flow from the source (impedance matching box) to the tip of the electrode. For the prototype, an insulated high voltage wire was soldered to a coax connector 57 on one end and to the electrode on the other; however, other commercially available methods may be used. With high voltage wire, RF shielding is provided inside the housing (not shown).

The source for the gas supply 22 is a standard tank of Helium, preferred at this time, although other gases and mixtures of gases will be used. The gas regulator 26 is set to provided a gas flow at 32 psi and the flow meter 28 is adjusted to provide flow rate between 5 to 10 standard cubic feet per hour. A connector formed from 1/8 inch Outside Diameter (OD) plastic tubing was utilized to connect the flow meter 28 to the hand held PDEB generator 20. A gas line connector 58 formed from a short section of 1/8 inch Inside Diameter (ID) tubing is mounted through the PDEB generator housing 42 and frictionally receives and retains the end of the 1/8 inch OD tubing. Within the housing 42, a length of 1/8 inch OD tubing 59 connects the brass tube electrode 36 to the inner end of the 1/8 inch OD connector 58.

Additional oscillators 30 are provided as needed for the particular application. While the invention contemplates that the RF generator 12 and any additional oscillators 30 generate sinusoidal time varying voltages, the invention also contemplates use of other power supplies such as, for example, pulsed DC, square wave, saw-tooth DC and 50 or 60 cycle AC. With regard to the additional oscillators, the invention contemplates that the RF generator 12 would supply a carrier frequency over which other frequencies are sent to the treatment surface. There are certain resonant frequencies which harm cells such as cancerous cells and other resonant frequencies that may be used to heal or strengthen cells. It is the intent of the present invention to overlay several of these frequencies, as needed, upon the 13.56 mHz carrier frequency. While prior art devices operated at higher voltages and currents, the present invention may be operated at 1,250 volts and 8 milliamps, a significant power reduction. The lower operating voltages and currents utilized with the present invention make possible the hand held device disclosed herein. Additionally, while 13.56 mHz is used in the description, frequencies in the range of 50 cycles to 900 mHz are contemplated for operation of the system 10 with 900 mHZ being used for tissue ablation.

It will be understood that the prototype system 10 described above is intended to be exemplary and that the present invention may be practiced using different materials and dimensions from that which are described above.

Figure 3:
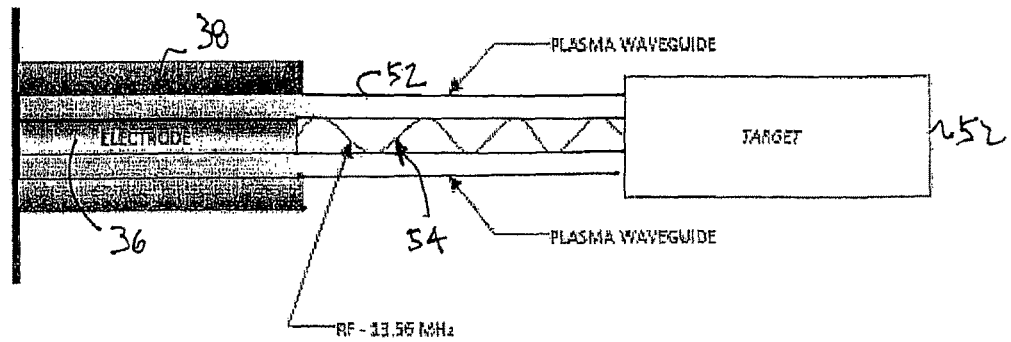
FIG. 3 illustrates the generation of a Plasma Directed Electron Beam by the system shown in FIG. 1.

As described above, electricity travels through the plasma guide to do the work, as illustrated in FIG. 3 where the operation of the PDEB generator 20 is illustrated. As shown in FIG. 3, a plasma sheath, or waveguide, 50 is generated and directed toward a target 52. The plasma sheath 50 contains and directs a coherent, non-axially propagating high energy electromagnetic wave 54. The plasma directed electron beam generated by the present invention differs from prior art plasma devices, generally, in that it serves to induce and maintain the high energy state of the surrounding and confining plasma it generates. This occurs irrespective of the distance the energized species travel away from the electrode and it further serves to excite the molecules of the surface materials to which it is directed. In traditional prior art plasma devices, the excitation takes place only at the discharge or excitation point of a plasma device and the energized species decay proportionally to the distance the plasma travels away from their discharge or excitation point.

Figure 4:
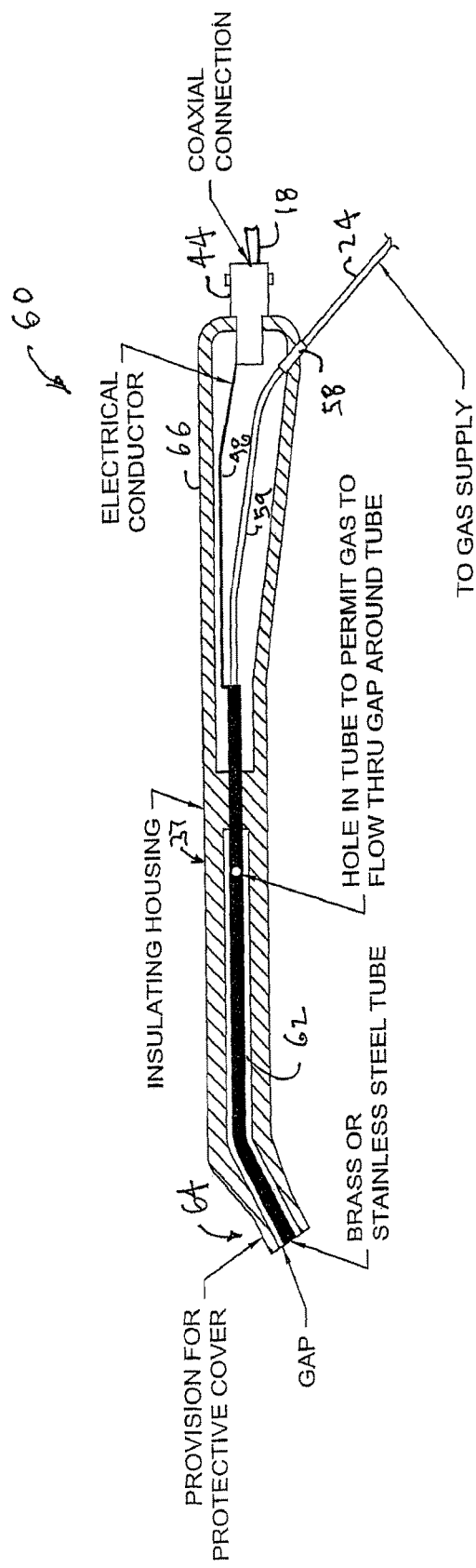
FIG. 4 is sectional view of a second embodiment of a PDEB generator that is included in the system shown in FIG. 1.

An alternate embodiment 60 of the PDEB generator is illustrated in FIG. 4 where components that are similar to components shown if FIGS. 1 and 2 have the same numerical identifiers. In the alternated embodiment 60, an angled brass or stainless steel electrode 62 is utilized with provision for the placement of a disposable protective cover 64 at the electrode tip end. This sketch also shows the molding of the insulating housing 66 to provide a gap around the electrode 62, replacing the quartz tubing used on the PDEB generator 20 shown in FIG. 2. The angled electrode 62 provides a more comfortable means of holding the apparatus and effectively covering the treatment area. FIG. 4 also shows the gas and electrical connections which are substantially the same as shown in FIGS. 1 and 2.

Figure 5:
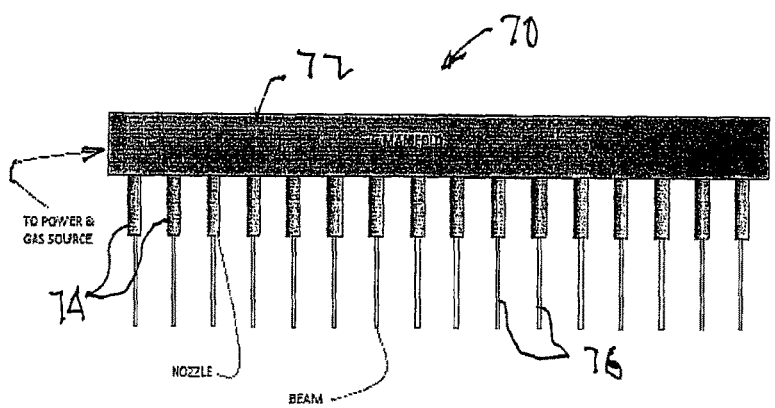
FIG. 5 illustrates another embodiment of the PDEB generator that may be included in the system shown in FIG. 1.
Figure 6:
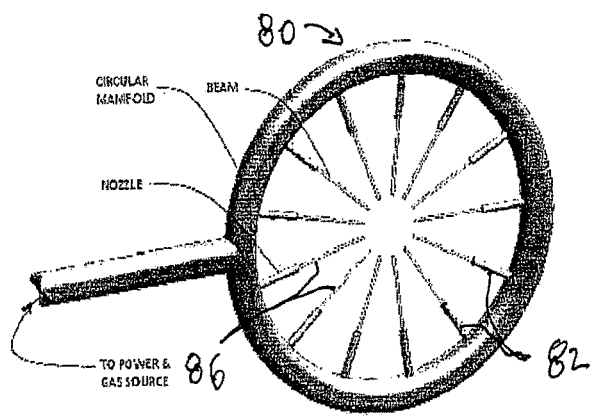
FIG. 6 illustrates another embodiment of the PDEB generator that may be included in the system shown in FIG. 1.

Another alternate embodiment 70 is shown in FIG. 5 that includes a linear manifold 72 upon which are mounted a plurality of nozzles 74. The configuration generates multiple parallel plasma/energy beams 76 for creating a sterilizing pathway over a treatment area having a width of one half to four or more inches wide.

Figure 8:
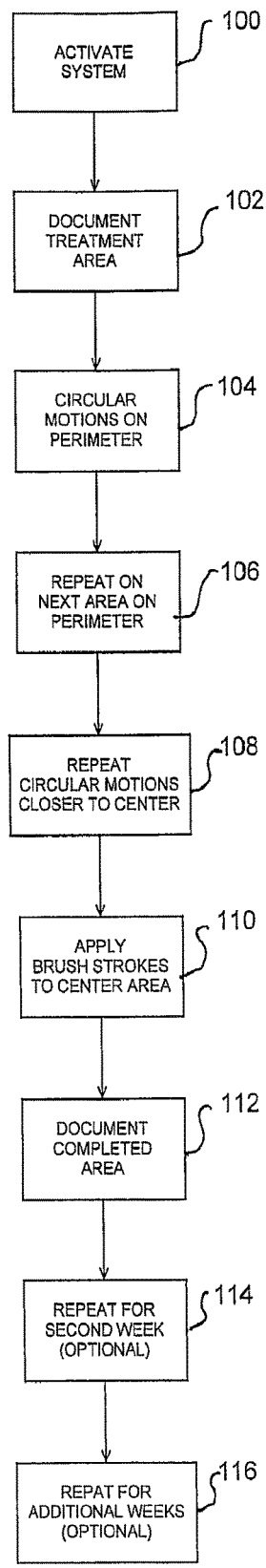
FIG. 8 is a flow chart for a method of operation for the PDEB system shown in FIG. 1.

Yet another alternate embodiment 80 is shown in FIG. 8 that includes a circular manifold 82 upon which are mounted a plurality of inward facing nozzles 84. The configuration generates multiple converging plasma/energy beams 86 for creating a sterilizing pathway over a treatment area having a diameter of one half to four or more inches. In both of the embodiments 70 and 80, a manifold carrying a plurality of spaced apart nozzles is utilized to spread a number of beams over a wide area. The particular pattern may be changed by changing the shape of the manifold to provide different beam patterns, such as, for example, a diamond shape or elliptical shape (not shown).

Figure 7:
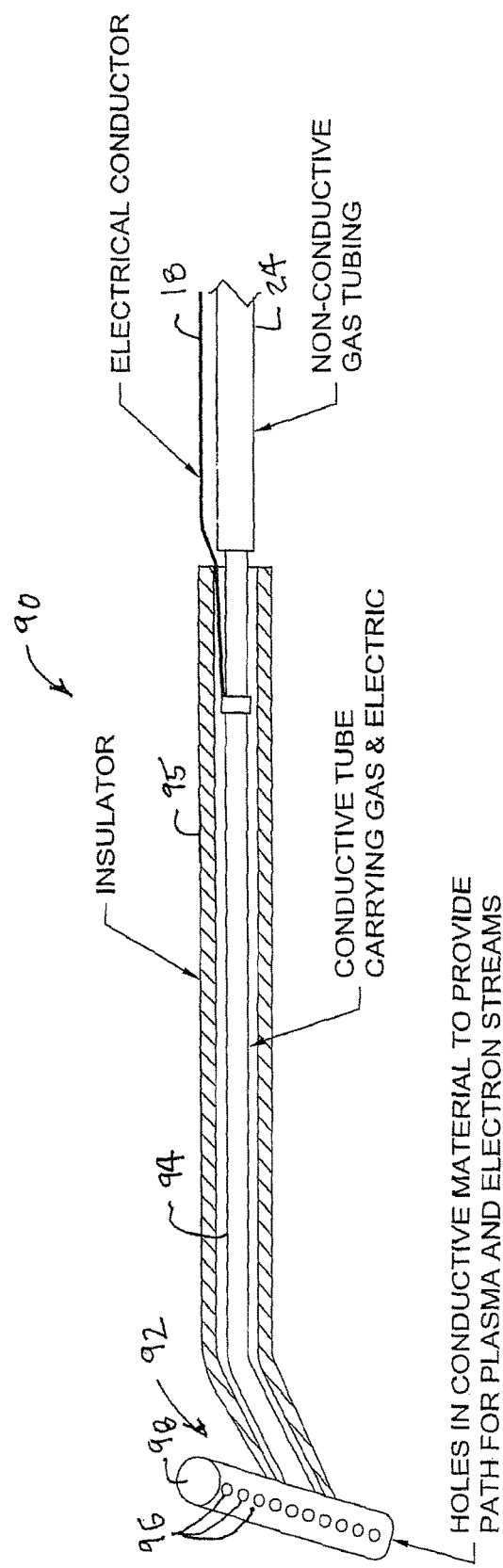
FIG. 7 illustrates another embodiment of the PDEB generator that may be included in the system shown in FIG. 1.

While a tubular electrode or a tube within a tube may be desirable where precise application and direction of the PDEB is required, the present invention also contemplates using a simple hole in a hollow conductor (not shown), properly sealed to retain gases required, that emits a cold plasma directed electron beam and multiple such beams. A variation of this embodiment is shown at 90 in FIG. 7. The illustrated embodiment 90 includes a tubular T-shaped hand held nozzle 92. A section of ⅜ inch tubing 94 is disposed within a generally tubular insulator 95, The tubing 94 is connected to the base of the T and carries gas to the nozzle. A plurality of apertures 96 are formed through the cross piece of the nozzle 92 and are operative to emit the plasma sheath and energy beam. End caps 98 seal the ends of the cross piece.

The method of operation of the system 10 will now be described in light of the flow chart shown in FIG. 8. In functional block 100, the system and the Helium or other inert or reactive gas supply is turned on. Upon beginning treatment, a photograph of the wound area is taken in functional block 102 and observations of the wound before treatment are noted. In functional block 104, the PDEB generator 20 is held much like a pencil or paintbrush and moved in a small circular motion, holding the tip of the PDEB generator about 2 millimeters from the surface of a wound. The initial motion is directed toward an area upon the outer perimeter of the wound area. The movement should be timed at about one revolution in one to two seconds, providing complete coverage of the first circular area on the wound.

After the first circle is completely exposed to the PDEB, the generator is moved to the next adjacent wound area in functional block 106 and the circular motion is repeated for one to two seconds. This pattern is duplicated until the entire perimeter area of the wound has been exposed to the PDEB with the area covered by each circular motion overlapping the area covered by previous circular motion.

Once the entire perimeter of the wound has been covered, in functional block 108, an area adjacent to the previously exposed area that is closer to the center of the wound is selected and the circular pattern of exposure is duplicated with a series of circular motions. The circular pattern with the circular motion of the apparatus is repeated until all areas surrounding the center of the wound have been exposed to the PDEB.

When the unexposed center of the wound area is approximately ¼" wide, the treatment advances to functional block 110 to begin a back and forth brushing motion with the apparatus starting at an edge of the unexposed wound area, brushing back and forth in a pattern to traverse the unexposed wound area until all of the remaining unexposed area has been exposed. Upon completion of the treatment, a second photograph of the wound area is taken in functional box 112 and after treatment observations of the wound are noted. The circular pattern and brushing pattern should be repeated every other day for the first week.

Exposure may be scheduled for every $3^{rd}$ day during the second week, depending upon progress of healing, as shown in functional block 114. Exposure may be continued for two additional weeks as determined by the physician, as shown in functional block 116.

The present invention dissociates the toxins secreted by dead pathogens and thereby lessens the bio-load residual in a wound area while also creating excited species in the plasma waveguide including electrons, photons, radicals, ions and neutrals. Ultra violet spectrum photons generated by the present invention enhance the coagulation of the blood in a wound area.

The present invention can utilize a gas combination consisting of an inert gas such as, for example, Helium, and 2% Oxygen to generate Atomic Oxygen. The Atomic Oxygen is then utilized at the wound site to accelerate healing.

The present invention reveals a number of improvements over prior art plasma beam devices and applies the improvements to a use not heretofore contemplated. This use involves the acceleration of the healing of wounds in humans and animals and the sterilization of the wound surfaces, instantly killing all pathogens including bacteria, bacteria spores, fungi, molds, prions and viruses. The present invention has been demonstrated to remove and heal the situs of basil cell carcinoma (skin cancer), without surgery, within a period of 34 days, all without damage to surrounding and underlying healthy cells and tissue. The present invention has been demonstrated to dissociate volatile organic compounds associated with wound care procedures. The present invention has been demonstrated to sterilize surfaces ancillary to the wound care environment which include porous and non-porous surfaces as well as hard and soft surfaces such as Styrofoam with no damage to such surfaces.

In summary, the present invention provides the following features: Acceleration of the healing of wounds in humans and animals; Sterilization of the wound surfaces, instantly killing all pathogens including bacteria, bacteria spores, fungi, molds, prions and viruses.

Dissociation of volatile organic compounds associated with wound care procedures.

Sterilization of surfaces ancillary to the wound care environment which include porous and non-porous surfaces as well as hard and soft surfaces such as Styrofoam with no damage to such surfaces.

Operation at power ranges between 5 Watts and 30 Watts which produce a cold, non-thermal plasma to serve as the waveguide for the radio frequency beam providing the emission of electrons to the intended target;

Causes no discomfort, pain or burns, when the beam produced by the system is directed toward the skin of a recipient, permitting the PDEB to pass across the wound area and healthy tissue without discomfort to the recipient or damage to healthy skin tissue;

Provides refined impedance matching procedures to permit this lower power operation with micro-currents and permit the use of a flexible conductor which can extend a distance from the tuning network enabling the portability of the handheld wound care device;

Removes and heals the situs of basil cell carcinoma (skin cancer), without surgery;

Allows the radio frequency wave to be "time shared" so that the PDEB can be emitted from multiple apertures along a conductor and along parallel paths or a circular path, simultaneously, from a single conductor and single source of energy;

Does not need a nozzle or tubular electrode in all applications of the technology. While a tubular electrode or a tube within a tube may be desirable where precise application and direction of the PDEB is required, a simple hole in a hollow conductor, properly sealed to retain gases required, will emit a cold plasma directed electron beam and multiple such beams;

Lower operating voltages and currents make possible the hand held device disclosed herein;

nozzles and manifolds can be configured in various shapes and forms, extending the work distance of this technology over larger areas and over irregularly shaped areas permitting larger area coverage at a minimal addition of energy;

The plasma directed electron beam generated by the present invention differs from prior art plasma devices, generally, in that it serves to maintain the high energy state of the surrounding and confining plasma it generates for the entire length of the beam. This occurs irrespective of the distance the charged species travel away from the electrode and it further serves to excite the molecules of the surface materials to which it is directed;

The Plasma Directed Electron Beam (PDEB) uses the electrical potential from a single electrode to generate sufficient plasma to serve as a waveguide for the transmission of a coherent, non-axially propagating electromagnetic wave at these low power settings;

The Plasma Directed Electron Beam (PDEB) creates photons which are directed to a wound site and penetrate the epidural layer of tissue;

The excitation to plasma state of inert and reactive gases directed to a wound site;

The present invention contemplates a means to provide multiple beams to cover larger wound site areas;

The present invention contemplates a means to provide a manifold with multiple beams to sterilize surface areas;

The present invention also may be utilized to produce atomic oxygen directed and direct same to the situs of a wound.

an apparatus that is hand held as described herein; a method to treat wounds and skin abnormalities as described herein any frequency can be used to generate the PDEB;

wave forms other than radio frequency can generate the PDEB, including square waves, saw tooth waves, pulsed direct current and direct current or any other wave form; and additional oscillators can be connected to the system which would provide additional resonant frequencies to the output of the PDEB, using the 13.56 mHz wave as a carrier frequency.

While any frequency may be used to generate the PDEB, 13.56 mHz is selected because the Federal Communications Commission has designated it as one of the Industrial, Scientific and Medical frequencies to be used.

This plasma directed electron beam differs from plasma devices, generally, in that it serves to maintain the high energy state of the surrounding and confining plasma it generates, irrespective of the distance the charged species travel away from the electrode and it further serves to excite the molecules of the surface materials to which it is directed. In traditional plasma devices, the excitation takes place only at the discharge or excitation point of a plasma device and the energized species decay proportionally to the distance the plasma travels away from their discharge or excitation point.

In accordance with the provisions of the patent statutes, the principle and mode of operation of this invention have been explained and illustrated in its preferred embodiment. For example, the embodiment of the PDEB generator shown in FIG. 2 may be modified with the replacement of the quartz tube 38 by an molded insulated housing that extends over the electrode 36, as illustrated in FIG. 4. However, it must be understood that this invention may be practiced otherwise than as specifically explained and illustrated without departing from its spirit or scope.

What is claimed is:
1. A device for treating wounds comprising:
a hollow electrode having a sealed end and an open end, and at least one aperture in the hollow electrode; the electrode being configured to generate an electron beam from the sealed end of the electrode;

the electrode being axially disposed within a tube, the tube being configured for establishing a shaped plasma sheath for directing the electron beam formed by the electrode;

the at least one aperture in the electrode being configured surface to permit flow of introduced gas through both the electrode and a surrounding gap formed between the electrode and the tube such that the gas flows in a laminar manner to establish a waveguide for the electron beam;

a gas supply connected to the open end of said electrode; and a power supply connected to said electrode for energization of said plasma sheath and establishment of said electron beam such that said plasma sheath contains and directs said electron beam, wherein the power supply is configured to power the device in a power range of from about 5 watts to about 30 watts.

2. The device according to claim 1 wherein said voltage supply includes one of a radio frequency oscillator, a pulsed DC generator, a square wave generator, a saw-tooth generator, a 50 cycle AC generator, a 60 cycle generator and a DC voltage supply.

3. The device according to claim 2 further including an impedance matching circuit connected between said electrode and said voltage source.

4. The device according to claim 3 wherein said impedance matching circuit includes at least one of an adjustable inductance and an adjustable capacitance.

5. The device according to claim 4 wherein said adjustable component is manually adjustable.

6. The device according to claim 4 wherein said adjustable component is automatically adjustable.

7. The device according to claim 3 further including at least one nozzle with said electrode and tube being disposed within said nozzle, said nozzle providing direction for said shaped plasma sheath.

8. The device according to claim 7, further including a manifold carrying the at least one nozzle and providing coverage over a surface area for said shaped plasma sheath.

9. The device according to claim 8 wherein a plurality of apertures are formed through the manifold.

10. A method for providing care of a wound comprising the steps of:
(a) providing the device of claim 1;
(b) energizing the electrode to establish a Plasma Directed Electron Beam (PDEB) and to create a supply of electrons and photons that are guided within the plasma sheath; and
(c) directing the PDEB toward a wound.

11. The method according to claim 10 wherein the electrode provided in step (a) is disposed within a hand held nozzle to allow direction of the PDEB.

12. The method according to claim 11 wherein the gas supply provides a mixture of oxygen and an inert gas, the gas cooperating with the PDEB to form atomic oxygen.

13. The method according to claim 11 wherein step (c) includes moving the nozzle with small circular motions over an area on the circumference of the wound and then linking a series of such movements in a generally spiral path toward the center of the wound and then completing the treatment with brush stroke movements across the center of the wound.

14. The method according to claim 10 wherein the electrode provided in step (a) is disposed within a manifold to allow direction of the PDEB over a surface area.

15. The method according to claim 11 wherein the method is used for the desiccation of dead pathogens to lessen the biological load in a wound area and thereby reduce the amount of fluids present in the wound area.

16. The method according to claim 11 wherein the method is used to enhance the healing of a wound area.

17. The method of claim 10, wherein the electrode generates sufficient energy such that the plasma sheath serves as a waveguide for transmission of a coherent, non-axially propagating electromagnetic wave.

18. The method of claim 10, wherein the device operates at 1,250 volts and 8 milliamps.

19. The method of claim 10, wherein the device operates at a frequency of about 13.56 mHz.

20. The method of claim 10, wherein the device operates at frequencies in the range of 50 to 900 mHz.

21. The method of claim 10, wherein the device includes at least one RF generator configured to supply a carrier frequency over which other frequencies are sent to the wound.

22. A method of enhancing the healing of wounds and skin surface abnormalities and to kill pathogens on a skin surface of a human or an animal, the method comprising the steps of:
(a) energizing an electrode axially contained within a tube to establish a stream of electrons and photons;
(b) providing a supply of gas to the tube to establish a cold plasma to contain and direct the stream of electrons and photons; and
(c) orienting the electrode to direct the stream of electrons and photons toward a skin surface of a human or an animal for enhancing the healing of wounds and skin surface abnormalities and to kill pathogens thereon.

* * * * *